United States Patent [19]

Muller et al.

[11] 4,276,417

[45] Jun. 30, 1981

[54] OXADIAZOLOTRIAZINE DERIVATIVES

[75] Inventors: Jean-Claude Muller, Rixheim, France; Henri Ramuz, Birsfelden, Switzerland

[73] Assignee: Hoffmann-La Roche Inc., Nutley, N.J.

[21] Appl. No.: 61,068

[22] Filed: Jul. 26, 1979

[30] Foreign Application Priority Data

Jul. 31, 1978 [CH] Switzerland ............ 8184/78
May 15, 1979 [CH] Switzerland ............ 4505/79

[51] Int. Cl.³ ............................................. C07D 498/04
[52] U.S. Cl. ....................................... 544/198; 542/420
[58] Field of Search ........................... 544/198; 542/420

[56] References Cited

U.S. PATENT DOCUMENTS

| 3,270,014 | 8/1966 | Ursprung et al. | |
|---|---|---|---|
| 3,475,430 | 10/1969 | Ursprung et al. | |
| 4,150,131 | 4/1979 | Muller et al. | 424/251 |
| 4,150,132 | 4/1979 | Muller et al. | 424/251 |

FOREIGN PATENT DOCUMENTS

| 1620637 | 8/1970 | Fed. Rep. of Germany . |
| 2804519 | 8/1978 | Fed. Rep. of Germany . |
| 6501753 | 8/1965 | Netherlands . |
| 6608725 | 1/1967 | Netherlands . |
| 6609268 | 1/1967 | Netherlands . |
| 6616988 | 6/1967 | Netherlands . |
| 1025902 | 2/1962 | United Kingdom . |
| 1053307 | 12/1966 | United Kingdom . |

*Primary Examiner*—John M. Ford
*Attorney, Agent, or Firm*—Jon S. Saxe; Bernard S. Leon; William G. Isgro

[57] ABSTRACT

Oxadiazolotriazine derivatives of the formula

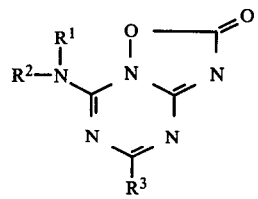

I wherein $R^1$, $R^2$ and $R^3$ are as hereinafter set forth, are described. The compounds of formula I are useful in the treatment of vascular-condition hypertension or also as vasodilators in the case of peripheral blood supply disorders.

15 Claims, No Drawings

OXADIAZOLOTRIAZINE DERIVATIVES

BRIEF SUMMARY OF THE INVENTION

The invention relates to oxadiazolotriazine derivatives of the formula

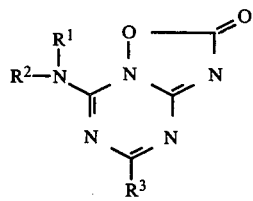

I wherein $R^1$ is hydrogen and $R^2$ is a group of the formula

—COOR$^5$ or —CH(R$^6$)COOR$^7$, or $R^1$ and $R^2$ are the same and are hydrogen or a group of the formula —CH(R$^6$)COOR$^7$; $R^3$ is diallylamino or 1,2,5,6-tetrahydropyridin-1-yl; wherein $R^4$ is alkyl, haloalkyl, alkoxyalkyl, aryloxyalkyl, aralkyloxyalkyl, aralkyl, alkoxycarbonylalkyl, aryl, a group of the formula —C(R$^8$)=CH(R$^9$), alkoxycarbonylalkylcarbonyl, or a 4-membered to 7-membered heterocyclic group which is optionally bound via a methylene group, $R^5$ is alkyl, alkoxyalkyl, aralkyl, aryl or allyl, $R^6$ is hydrogen or alkyl, $R^7$ is alkyl and $R^8$ and $R^9$ each are alkyl, aryl or aralkyl or a 4-membered to 7-membered heterocyclic group, and salts with pharmaceutically acceptable bases.

DETAILED DESCRIPTION OF THE INVENTION

The oxadiazolotriazine derivatives of the invention are compounds of the formula

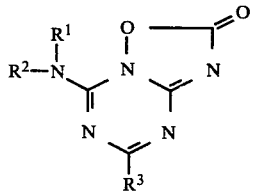

I wherein $R^1$ is hydrogen and $R^2$ is a group of the formula

—COOR$^5$ or —CH(R$^6$)COOR$^7$, or $R^1$ and $R^2$ are the same and are hydrogen or a group of the formula —CH(R$^6$)COOR$^7$, $R^3$ is diallylamino or 1,2,5,6-tetrahydropyridin-1-yl, $R^4$ is alkyl, haloalkyl, alkoxyalkyl, aryloxyalkyl, aralkyloxyalkyl, aralkyl, alkoxycarbonylalkyl, aryl, a group of the formula —C(R$^8$)=CH(R$^9$), an alkoxycarbonylalkylcarbonyl, or a 4-membered to 7-membered heterocyclic group which is optionally bound via a methylene group, $R^5$ is alkyl, alkoxyalkyl, aralkyl, aryl or allyl, $R^6$ is hydrogen or alkyl, $R^7$ is alkyl and $R^8$ and $R^9$ each are alkyl, aryl or aralkyl or a 4-membered to 7-membered heterocyclic group, or a salt thereof with a pharmaceutically acceptable base.

The term "alkyl" as used herein, alone or in combination, denotes a straight-chain and branched-chain saturated hydrocarbon group of 1-8 carbon atoms, for example, methyl, ethyl, n-propyl, isopropyl, n-butyl, isobutyl, tert.butyl, or the like. The term "alkoxy" denotes an alkyl ether wherein the "alkyl" moiety is as described above. The term "haloalkyl" denotes an alkyl group wherein one or more of the hydrogen atoms has been replaced by "halogen". The term "halogen" denotes fluorine, chlorine, bromine or iodine. The term "aryl" denotes mononuclear or dinuclear aromatic groups of up to 12 carbon atoms in which one or more of the hydrogen atoms can be replaced by alkyl, alkoxy, halogen, cyano, nitro, alkanoyloxy or alkoxycarbonyl, for example, phenyl, halophenyl, dihalophenyl, methoxyphenyl, dimethoxyphenyl, nitrophenyl, tolyl, methoxycarbonylphenyl, naphthyl and the like. The term "aryloxy" denotes an aryl ether-group in which the "aryl" moiety is as previously described. The term "aralkyl" denotes an arylalkyl group such as benzyl, phenethyl and the like. The term "aralkyloxy" denotes an arylalkyl ether group such as benzyloxy, phenethyloxy and the like. The term "4-membered to 7-membered heterocyclic group" includes saturated and unsaturated heterocyclic groups containing one or more hetero atoms selected from nitrogen, oxygen and sulfur, exemplary of such groups are furyl, nicotinyl, isonicotinyl, pyridyl, thienyl, pyrrolinyl, piperidinyl and the like. The term "alkanoyloxy" denotes an acyloxy moiety derived from formic acid or from an alkanecarboxylic acid. The alkyl moiety of the alkanecarboxylic acid contains 1-7, preferably 1-3, carbon atoms. Thus, examples of alkanoyloxy groups are formyloxy, acetoxy, propionyloxy, butyryloxy and the like.

Preferred compounds of formula I are those wherein $R^3$ is a diallylamino group. More preferred are those compounds of formula I wherein $R^1$ is hydrogen and $R^2$ is hydrogen or a group of the formula

Especially preferred are those compounds of formula I wherein $R^4$ is aryl, alkoxyalkyl, a group of the formula —C(R$^8$)=CH(R$^9$) or a 4-membered to 7-membered heterocyclic group which is optionally bound via a methylene group. Most especially preferred are those compounds of formula I wherein $R^4$ is phenyl, methoxymethyl, ethoxymethyl, a group of the formula —C(CH$_3$)=CH$_2$ or —C(CH$_3$)=CH—CH$_3$, or furyl.

From the foregoing it will be appreciated that those compounds of formula I wherein $R^3$ is diallylamino, $R^1$ is hydrogen, $R^2$ is hydrogen or a group of the formula

wherein $R^4$ is phenyl, methoxymethyl, ethoxymethyl, a group of the formula —C(CH$_3$)=CH$_2$ or —C(CH$_3$)=CH—CH$_3$, or furyl, are especially preferred.

Especially preferred compounds of formula I are:
N-{5-Diallylamino-2-oxo-2H-[1,2,4]oxadiazolo[2,3-a]-s-triazin-7-yl}benzamide;

N-{5-diallylamino-2-oxo-2H-[1,2,4]oxadiazolo[2,3-a]-s-triazin-7-yl}-2-methoxyacetamide;

2-ethoxy-N-{5-diallylamino-2-oxo-2H-[1,2,4]oxadiazolo[2,3-a]-s-triazin-7-yl}-acetamide;

N-{5-diallylamino-2-oxo-2H-[1,2,4]oxadiazolo[2,3-a]-s-triazin-7-yl}-2-methylacrylamide;

N-{5-diallylamino-2-oxo-2H-[1,2,4]oxadiazolo[2,3-a]-s-triazin-7-yl}-2-furamide;

7-amino-5-diallylamino-2H-[1,2,4]oxadiazolo[2,3-a]-s-triazin-2-one; and

N-{5-diallylamino-2-oxo-2H-[1,2,4]oxadiazolo[2,3-a]-s-triazin-7-yl}-3-methylcrotonamide.

According to the process of the invention, the oxadiazolotriazine derivatives, that is, the compounds of formula I and their salts, can be prepared by (a) to prepare compounds of formula I wherein $R^1$ and $R^2$ each are hydrogen and $R^3$ is as previously described, reacting a compound of the formula

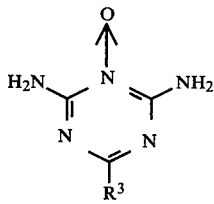

wherein $R^3$ is as previously described, with phosgene, or (b) to prepare compounds of formula I wherein $R^1$ is hydrogen, $R^2$ is a group of the formula

wherein $R^4$ is as previously described, and $R^3$ is as previously described, reacting a compound of the formula

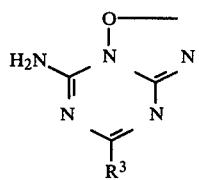

wherein $R^3$ is as previously described, with an acylating agent which provides a group of the formula

or (c) to prepare compounds of formula I wherein $R^1$ is hydrogen, $R^2$ is a group of the formula $-COOR^5$, wherein $R^5$ is as previously described, and $R^3$ is as previously described, reacting a compound of formula Ia with a chloroformic acid ester of the formula

wherein $R^5$ is as previously described, or (d) to prepare compounds of formula I wherein $R^1$ is hydrogen, $R^2$ is a group of the formula $-COOR^5$, wherein $R^5$ is as previously described, and $R^3$ is as previously described, cyclizing a compound of the formula

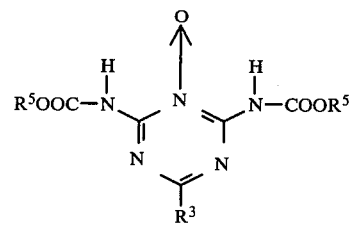

wherein $R^3$ and $R^5$ are as previously described, or (e) to prepare compounds of formula I wherein $R^1$ is hydrogen, $R^2$ is a group of the formula $-CH(R^6)COOR^7$, and $R^3$ is as previously described, reacting a compound of formula Ia with a compound of the formula

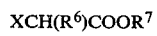

wherein X is halogen and $R^6$ and $R^7$ are as previously described, or (f) to prepare compounds of formula I wherein $R^1$ and $R^2$ each are a group of the formula $-CH(R^6)COOR^7$ and $R^3$ is as previously described, reacting a compound of the formula

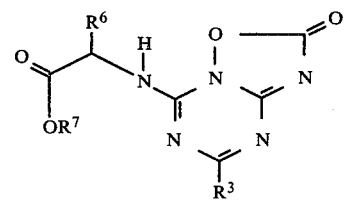

wherein $R^3$, $R^6$ and $R^7$ are as previously described, with a compound of formula V, and (g) if desired, converting a compound of formula I obtained into a salt or converting a salt into a different salt.

The reaction of a compound of formula II with phosgene in accordance with process embodiment (a) is carried out in a known manner in the presence of a solvent or solvent mixture. Exemplary of solvents which can be used are aromatic hydrocarbons such as benzene, toluene and xylene; chlorinated hydrocarbons such as methylene chloride and chloroform; dimethylformamide; and the like or mixtures thereof. The reaction is conveniently carried out at atmospheric pressure and at a temperature in the range of from about $-20°$ C. to $50°$ C., preferably in the range of from about $0°$ C. to room temperature, in the presence of an acid-binding agent. Suitable acid-binding agents are tertiary organic bases such as triethylamine, ethyldiisopropylamine and pyridine, or inorganic bases, for example, alkali metal hydroxides, such as sodium hydroxide and potassium hydroxide; alkaline earth metal hydroxides, such as barium hydroxide and calcium hydroxide; carbonates, such as potassium carbonate and sodium carbonate; bicarbonates, such as sodium bicarbonate, and the like.

The acylation of a compound of formula Ia in accordance with process embodiment (b) is also carried out according to known methods. Suitable acylating agents are activated acid derivatives such as acid halides or acid anhydrides of the formulas $R^4-COX$ and $(R^4-$ CO)₂O. The reaction is carried out in an inert solvent or solvent mixture at a temperature in the range of from about 0° C. to 70° C., preferably in the range of from about 0° C. to 30° C., more preferably at room temperature, in the presence of an acid-binding agent. Examples of inert solvents which can be used are aromatic hydrocarbons such as benzene, toluene and xylene; chlorinated hydrocarbons such as methylene chloride and chloroform; ethers such as tetrahydrofuran and dioxane; dimethylformamide; dimethylsulfoxide; hexamethylphosphoric acid triamide and the like. Suitable acid-binding agents are tertiary organic bases such as triethylamine, ethyldiisopropylamine and pyridine, or inorganic bases, for example, alkali metal hydroxides, such as sodium hydroxide and potassium hydroxide, alkaline earth metal hydroxides, such as barium hydroxide and calcium hydroxide; carbonates, such as potassium carbonate and sodium carbonate; bicarbonates, such as sodium bicarbonate, and the like.

The reaction of a compound of formula Ia with a chloroformic acid ester of formula III in accordance with process embodiment (c) is carried out in an inert solvent or solvent mixture in the presence of an acid-binding agent. Suitable solvents for the present purpose are chlorinated hydrocarbons such as methylene chloride and chloroform; ethers such as diethyl ether, tetrahydrofuran and dioxane; dimethylformamide; and the like or mixtures thereof. The reaction can also be carried out in a water-containing solvent or in the presence of water in a two-phase system, for example, methylene chloride/water. Examples of acid-binding agents which can be used are bases such as triethylamine, ethyldiisopropylamine, dimethylamine, pyridine, alkali hydroxides and the like. When the reaction is carried out in the presence of a liquid base, the latter can also serve as the solvent. The reaction is conveniently carried out at a temperature in the range of about −10° C. and room temperature, preferably between about 0° C. and 10° C.

The cyclization of a compound of formula IV in accordance with process embodiment (d) is carried out in a known manner by heating to a temperature in the range of from about 50° C. to 200° C., preferably in the range of from about 100° C. to 150° C. The cyclization can be carried out in the absence or presence of a solvent or solvent mixture. If the cyclization is carried out in a solvent or solvent mixture, then there can be used as the solvent aromatic hydrocarbons such as benzene, toluene and xylene; chlorinated hydrocarbons such as chloroform; alcohols such as butanol or isobutanol; ethers such as dibutyl ether, dioxane or diethyleneglycol dimethyl ether; dimethylformamide; dimethylsulfoxide; and the like or mixtures thereof. It will be appreciated that there can either be used a solvent whose boiling point lies higher than the cyclization temperature, or that there can be used a solvent boiling in the temperature range mentioned earlier at its reflux temperature. The cyclization is preferably carried out using dimethylformamide or toluene as the solvent. The cyclization time depends on the temperature at which the cyclization is carried out and lies in the range of from about 0.24 hour to 18 hours. If the cyclization is carried out in the preferred temperature range of from about 100° C. to 150° C., then the cyclization time is in the range of about 0.25 hour to 12 hours, preferably from 0.25 hour to 2 hours. When an alcohol is used as the solvent, it will be appreciated that, if a transesterification is to be avoided, the alcohol must correspond to the alcohol component present in the starting material utilized. In another especially preferred aspect, the cyclization is carried out in the presence of a base, in which case the temperature can be maintained substantially lower. In this aspect, the cyclization is preferably carried out at a temperature in the range of from about 0° C. to 80° C., conveniently at room temperature. Suitable bases are inorganic bases, for example, alkali metal hydroxides, such as sodium hydroxide and potassium hydroxide; alkaline earth metal hydroxides, such as barium hydroxide and calcium hydroxide, carbonates, such as potassium carbonate and sodium carbonate; and bicarbonates, such as sodium bicarbonate; or organic bases, such as dimethylamine, triethylamine, ethyldiisopropylamine and the like. When a base is used, the cyclization is carried out in a suitable inert solvent or solvent mixture. As the solvent there can be used the solvents referred to hereinbefore. When an inorganic base is used, the cyclization is conveniently carried out in a water-containing solvent mixture or in the presence of water in a two-phase system, for example, methylene chloride/water. When it is desired to bring about an intentional trans-esterification, the cyclization is preferably carried out in the presence of a base.

The reaction of a compound of formula Ia or Ib with a compound of formula V in accordance with process embodiment (e) or (f) is carried out according to known methods in an inert solvent such as acetone, methanol, tetrahydrofuran, dimethylformamide, hexamethylphosphoric acid triamide and the like, in the presence of an acid-binding agent such as potassium carbonate, sodium carbonate, triethylamine, ethyldiisopropylamine and the like, at a temperature in the range of from about 0° C. to 50° C., preferably at room temperature. In a preferred aspect, the reaction is carried out in acetone in the presence of potassium carbonate at room temperature.

The starting material of formula II wherein $R^3$ is diallylamino is known. The starting material of formula II wherein $R^3$ is 1,2,5,6-tetrahydropyridin-1-yl is new and also forms part of the invention, and can be prepared in an analogous manner to the preparation of the known compound. Two processes are illustrated in the following Formula Scheme. Regarding the precise reaction conditions, reference is made to the detailed Examples hereinafter.

Formula Scheme

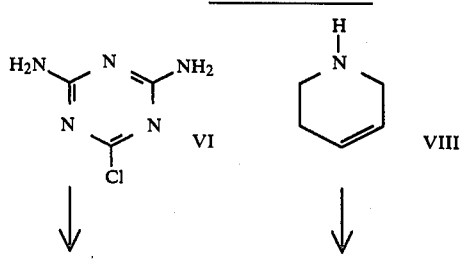

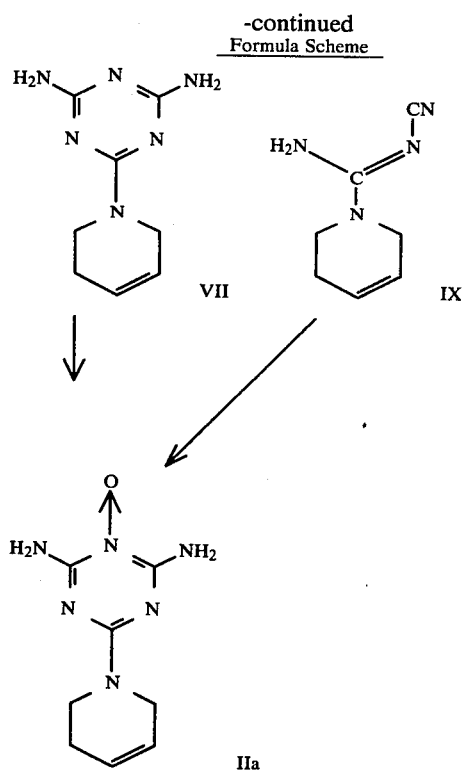

The starting materials of formula IV are new and also form part of the invention. They can be prepared by reacting a compound of formula II with a chloroformic acid ester of formula III. The reaction is carried out under the conditions described earlier in connection with the reaction of a compound of formula Ia with a chloroformic acid ester of formula III.

The compounds of formula I can be converted into salts; for example, by treatment with an inorganic base, for example, alkali metal hydroxide, such as sodium hydroxide and potassium hydroxide; an alkaline earth metal hydroxide, such as calcium hydroxide, or with an organic base such as monoalkylamine, such as methylamine, a dialkylamine, such as dimethylamine, a trialkylamine, such as triethylamine, a basic amino acid, such as arginine, piperidine, an azabicyclooctane or -nonane, for example, 3-azabicyclo[3.2.1]octane or 3-azabicyclo[3.2.2]nonane, and the like. Salts of the compounds of formula I can also be prepared by double-decomposition of a suitable salt. Among the salts of the compounds of formula I the pharmaceutically acceptable salts are preferred.

The oxadiazolotriazine derivatives of the invention possess long-lasting and valuable vasodilating and/or blood pressure-lowering properties and, accordingly, can be used for the treatment of vascular-condition hypertension or also as vasodilators in the case of peripheral blood supply disorders.

The blood pressure-lowering activity can be determined in conscious, female dogs by the following method:

The arterial blood pressure is measured oscillometrically and the heart frequency palpatorically by means of a surgically implanted carotid loop. After determination of the basic values, the substance to be tested is administered with a stomach probe to the dogs which have been fasted overnight. The individual dosages are administered cumulatively at an interval of one day in each case. The arterial blood pressure and the heart frequency are measured 0.5, 1, 1.5, 3, 6 and 22 hours after each administration. The dogs are observed as to their behavior during the duration of the experiment and for an additional 2 days after the last administration of test substance.

The blood pressure-lowering activity can also be determined in conscious, spontaneous hypertensive rats by the following method:

The systolic blood pressure and the heart frequency are measured twice before administration of the test substance. The test substance is administered by means of an oesophageal probe twice daily, morning and afternoon. Both parameters are measured at 1, 3, 6 and 24 hours after the administration and the percentage variations to the control values are calculated. The systolic blood pressure is measured indirectly in the tail artery of the rat by the method of Gerold et al. (Helv. Physiol. Acta 24: 58-69, 1966; Arzneimittelforschung 18: 1285-1287, 1968).

The results obtained using N-{5-diallylamino-2-oxo-2H-[1,2,4]oxadiazolo[2,3-a]-s-triazin-7yl}benzamide as the test substance are given in the following Tables, in each case the average values from 5 experiments are given.

TABLE I

| Dosage mg/kg p.o. | Hours after administration of test substance | | | | | | |
|---|---|---|---|---|---|---|---|
| | 0[1] | 0.5 | 1.0 | 1.5 | 3.0 | 6.0 | 22 |
| | Blood pressure Δ% (mm Hg) | | | | | | |
| 1.0 | 135 ± 1.3 | −2.2 ± 1.5 | −3.2 ± 2.8 | −2.2 ± 1.5 | −3.2 ± 3.8 | −3.2 ± 2.6 | −3.2 ± 2.1 |
| 3.0 | 135 ± 1.3 | −8.2 ± 5.7 | −9.2 ± 6.4 | −8.2 ± 6.3 | −8.2 ± 5.5 | −10.2 ± 3.5 | −8.0 ± 3.0 |
| 10.0 | 135 ± 1.3 | −15.2 ± 3.4 | −18.2 ± 3.8 | −20.2 ± 5.0 | −22.2 ± 6.4 | −15.2 ± 5.5 | −13.2 ± 4.0 |
| 30.0 | 135 ± 1.3 | −21.2 ± 1.3 | −22.2 ± 2.3 | −26.2 ± 1.9 | −21.2 ± 3.7 | −18.2 ± 4.4 | −13.8 ± 1.5 |
| | Heart frequency Δ% | | | | | | |
| 1.0 | 80 ± 1.8 | 2.2 ± 3.2 | 3.0 ± 2.3 | 1.8 ± 3.0 | 3.8 ± 2.2 | 7.0 ± 6.3 | 14.8 ± 9.9 |
| 3.0 | 80 ± 1.8 | 21.8 ± 10.1 | 27.0 ± 14.6 | 26.2 ± 14.3 | 29.0 ± 13.6 | 43.4 ± 16.3 | 51.0 ± 7.9 |
| 10.0 | 80 ± 1.8 | 56.2 ± 6.1 | 56.5 ± 5.6 | 62.5 ± 5.0 | 65.8 ± 6.3 | 60.5 ± 14.7 | 69.2 ± 2.3 |
| 30.0 | 80 ± 1.8 | 72.2 ± 7.7 | 71.0 ± 9.6 | 71.8 ± 8.2 | 72.2 ± 6.9 | 73.4 ± 7.5 | 57.0 ± 9.8 |

[1]Basic value

TABLE II

| Dosage mg/kg p.o. | Δ% Blood pressure | Δ% Heart frequency | Duration of activity in hours |
|---|---|---|---|
| 1.0 | −15.0% | +7.2% | >24 |
| 3.0 | −21.6% | +7.1% | >24 |
| 10.0 | −32.8% | +22.1% | >24 |
| 30.0 | −45.0% | +26.5% | >24 |

The compounds of formula I and their pharmaceutically acceptable salts can be used as medicaments; for example, in the form of pharmaceutical preparations which contain them in association with a compatible pharmaceutical carrier. Such carrier can be an organic or inorganic inert carrier material suitable for enteral or parenteral administration, for example, water, gelatin, gum arabic, lactose, starch, magnesium stearate, talc, vegetable oils, polyalkyleneglycols, or the like. The pharmaceutical preparations can be made up in a solid form, for example, as tablets, dragees, suppositories or capsules, or in a liquid form, for example, as solutions, suspensions or emulsions. The pharmaceutical preparations may be sterilized and/or may contain adjuvants such as preserving, stabilizing, wetting or emulsifying agents, salts for varying the osmotic pressure or buffers. They can also contain still other therapeutically valuable substances.

The daily dosage in the case of oral administration is in the range of from 10 mg. to 500 mg. and in the case of intravenous administration is in the range of from about 1 mg. to 50 mg. It will be appreciated that these dosages are given by way of examples and can be altered according to the severity of the condition to be treated and according to the judgement of the attending practitioner.

The Examples which follow further illustrate the invention. All temperatures are in degrees Centigrade, unless otherwise mentioned. The melting points are not corrected.

EXAMPLE 1

Preparation of 7-amino-5-diallylamino-2H-[1,2,4]oxadiazolo[2,3-a]-s-triazin-2-one 75 g. of 2,4-diamino-6-diallylamino-s-triazine-3-oxide are suspended in 800 ml. of methylene chloride and cooled while stirring to 0° C. At this temperature there are then simultaneously added dropwise within 45 minutes 180 ml. of 20% phosgene in toluene and sufficient 10% sodium hydroxide to hold the pH at 7-7.5. The mixture is subsequently stirred for a further 1 hour. Methylene chloride and methanol are then added in order to dissolve the precipitated product. The two phases are separated and the aqueous phase is extracted twice with methylene chloride. The combined organic extracts are dried over magnesium sulfate and evaporated under reduced pressure, there being obtained 7-amino-5-diallylamino-2H-[1,2,4]oxadiazolo[2,3-a]-s-triazin-2-one, having a melting point of 211°-213° C.

EXAMPLE 2

Preparation of pure ethyl 5-diallylamino-2-oxo-2H-[1,2,4]oxadiazolo[2,3-a]-s-triazine-7-carbamate 6 g. of diethyl 6-diallylamino-s-triazine-2,4-dicarbamate-3-oxide are suspended in 120 ml. of dimethylformamide and warmed to 140° C. for 20 minutes under an argon atmosphere and while stirring. The solvent is then evaporated off under reduced pressure and the residue is recrystallized from methylene chloride/ethanol/diethyl ether, there being obtained pure ethyl 5-diallylamino-2-oxo-2H-[1,2,4]oxadiazolo[2,3-a]-s-triazine-7-carbamate, having a melting point of 172°-174° C.

In an analogous manner, from 4.4 g. of dimethyl 6-diallylamino-s-triazine-2,4-dicarbamate-3-oxide, there is obtained methyl 5-diallylamino-2-oxo-2H-[1,2,4]oxadiazolo[2,3-a]-s-triazine-7-carbamate, having a melting point of 184°-185° C.; and from 5.9 g. of diisobutyl 6-diallylamino-s-triazine-2,4-dicarbamate-3-oxide, there is obtained isobutyl-5-diallylamino-2-oxo-2H-[1,2,4]oxadiazolo[2,3-a]-s-triazine-7-carbamate, having a melting point of 160°-162° C.

The diethyl 6-diallylamino-s-triazine-2,4-dicarbamate-3-oxide used as the starting material can be prepared as follows:

5.0 g. of 2,4-diamino-6-diallylamino-s-triazine-3-oxide are suspended in 200 ml. of methylene chloride and 20 ml. of triethylamine and treated at 0° C. while stirring with 8 ml. of ethyl chloroformate in 25 ml. of methylene chloride. After stirring for 1 hour at 0° C., the mixture is washed with water and the organic phase is dried over sodium sulfate and evaporated to dryness under reduced pressure. The residue is recrystallized from methylene chloride and ethanol, there being obtained pure diethyl 6-diallylamino-s-triazine-2,4-dicarbamate-3-oxide, having a melting point of 123°-125° C.

In an analogous manner, from 5.0 g. of 2,4-diamino-6-diallylamino-s-triazine-3-oxide and 5 ml. of methyl chloroformate there is obtained dimethyl 6-diallylamino-s-triazine-2,4-dicarbamate-3-oxide, having a melting point of 158°-160° C.; and from 5.0 g. of 2,4-diamino-6-diallylamino-s-triazine-3-oxide and 7 ml. of isobutyl chloroformate there is obtained diisobutyl 6-diallylamino-s-triazine-2,4-dicarbamate-3-oxide, having a melting point of 90°-92° C.

EXAMPLE 3

Preparation of pure isobutyl 5-diallylamino-2-oxo-2H-[1,2,4]oxadiazolo[2,3-a]-s-triazine-7-carbamate 18 g. of diisobutyl 6-diallylamino-s-triazine-2,4-dicarbamate-3-oxide are dissolved while stirring in 560 ml. of methylene chloride and treated with 1800 ml. of water and sufficient concentrated sodium hydroxide so that the pH value of the mixture amounts to 12.7. The mixture is then stirred for 75 minutes and the two phases are separated. The alkaline-aqueous phase is adjusted to pH 4 with 3-N hydrochloric acid and then extracted three times with methylene chloride. The organic extracts are dried over sodium sulfate and evaporated under reduced pressure. The residue is recrystallized from methylene chloride and diethyl ether, there being obtained pure isobutyl 5-diallylamino-2-oxo-2H-[1,2,4]oxadiazolo[2,3-a]-s-triazine-7-carbamate having a melting point of 161°-163° C.

EXAMPLE 4

Preparation of pure benzyl 5-diallylamino-2-oxo-2H-[1,2,4]oxadiazolo[2,3-a]-s-triazine-7-carbamate 4.0 g. of 7-amino-5-diallylamino-2H-[1,2,4]oxadiazolo[2,3-a]-s-triazin-2-one are suspended in 50 ml. of methylene chloride and 5 ml. of triethylamine and cooled to 0° C. 5 ml. of benzyl chloroformate are slowly added dropwise while stirring. The mixture is then stirred at 0° C. for 1 hour, subsequently treated with water and adjusted to pH 4 with 2-N hydrochloric acid. The aqueous phase is extracted twice with methylene chloride and the combined organic extracts are dried over sodium sulfate and evaporated. The residue is recrystallized from methylene chloride and diethyl ether, there being obtained pure benzyl 5-diallylamino- 2-oxo-2H-[1,2,4]oxadiazolo[2,3-a]-s-triazine-7-carbamate, having a melting point of 171°–173° C.

In an analogous manner, from 4.6 g. of 7-amino-5-diallylamino-2H-[1,2,4]oxadiazolo[2,3-a]-s-triazin-2-one and 4 ml. of butyl chloroformate there is obtained pure butyl 5-diallylamino-2-oxo-2H-[1,2,4]oxadiazolo[2,3-a]-s-triazine-7-carbamate having a melting point of 135°–137° C.;

from 2.0 g. of 7-amino-5-diallylamino-2H-[1,2,4]oxadiazolo[2,3-a]-s-triazin-2-one and 3 ml. of 2-methoxyethyl chloroformate there is obtained pure 2-methoxyethyl 5-diallylamino-2-oxo-2H-[1,2,4]oxadiazolo[2,3-a]-s-triazine-7-carbamate having a melting point of 171°–173° C.; and from 4.0 g. of 7-amino-5-diallylamino-2H-[1,2,4]oxadiazolo[2,3-a]-s-triazin-2-one and 5 ml. of allyl chloroformate there is obtained pure allyl 5-diallylamino-2-oxo-2H-[1,2,4]oxadiazolo[2,3-a]-s-triazine-7-carbamate having a melting point of 173°–175° C.

EXAMPLE 5

Preparation of
N-{5-diallylamino-2-oxo-2H-[1,2,4]oxadiazolo[2,3-a]-s-triazin-7-yl}-2-phenyl-acetamide 4.5 g. of 7-amino-5-diallylamino-2H-[1,2,4]oxadiazolo[2,3-a]-s-triazin-2-one are suspended in 100 ml. of methylene chloride and 10 ml. of triethylamine. 4.8 ml. of phenylacetyl chloride in 30 ml. of methylene chloride are added dropwise while stirring and cooling. The mixture is then stirred at room temperature for 70 minutes, treated with water and adjusted to pH 4 with 3-N hydrochloric acid. The two phases are separated and the aqueous phase is extracted with methylene chloride. The combined organic extracts are dried over sodium sulfate and evaporated to dryness under reduced pressure. The residue is recrystallized from methylene chloride and diethyl ether, there being obtained N-{5-diallylamino-2-oxo-2H-[1,2,4]oxadiazolo[2,3-a]-s-triazin-7-yl}-2-phenyl-acetamide having a melting point of 165°–167° C.

In an analogous manner, from 4.5 g. of 7-amino-5-diallylamino-2H-[1,2,4]oxadiazolo[2,3-a]-s-triazin-2-one and 10.8 g. of homoveratric acid chloride there is obtained N-{5-diallylamino-2-oxo-2H-[1,2,4]oxadiazolo[2,3-a]-s-triazin-7-yl}-2-(3,4-dimethoxyphenyl)-acetamide having a melting point of 139°–141° C.

EXAMPLE 6

Preparation of
2,4-dichloro-N-{5-diallylamino-2-oxo-2H-[1,2,4]oxadiazolo[2,3-a]-s-triazin-7-yl}benzamide 4.5 g. of 7-amino-5-diallylamino-2H-[1,2,4]oxadiazolo[2,3-a]-s-triazin-2-one are suspended in 100 ml. of methylene chloride and 10 ml. of triethylamine, cooled while stirring to about 5° C. and treated with 2.5 ml. of 2,4-dichlorobenzoyl chloride in 20 ml. of methylene chloride. After 1 hour at 0° C., the mixture is diluted with 100 ml. of water and adjusted to pH 4 with hydrochloric acid. The two phases are separated and the aqueous phase is extracted twice with methylene chloride. The combined organic extracts are dried over sodium sulfate and evaporated to dryness under reduced pressure. The residue is chromatographed over silica gel using a mixture of chloroform and methanol (99:1) for the elution. Crystallization of the residue from chloroform and diethyl ether yields 2,4-dichloro-N-{5-diallylamino-2-oxo-2H-[1,2,4]oxadiazolo[2,3-a]-s-triazin-7-yl}benzamide having a melting point of 163°–164° C.

In an analogous manner, from 4.3 g. of 7-amino-5-diallylamino-2H-[1,2,4]oxadiazolo[2,3-a]-s-triazin-2-one and 4.8 g. of 3,4-dichlorobenzoyl chloride there is obtained pure 3,4-dichloro-N-{5-diallylamino-2-oxo-2H-[1,2,4]oxadiazolo[2,3-a]-s-triazin-7-yl}benzamide having a melting point of 190°–191° C.; and from 4.5 g. of 7-amino-5-diallylamino-2H-[1,2,4]oxadiazolo[2,3-a]-s-triazin-2-one and 7.2 g. of 3,5-dimethoxybenzoyl chloride there is obtained pure N-{5-diallylamino-2-oxo-2H-[1,2,4]oxadiazolo[2,3-a]-s-triazin-7-yl}-3,5-dimethoxybenzamide having a melting point of 161°–164° C.

EXAMPLE 7

Preparation of pure
2,6-dichloro-N-{5-diallylamino-2-oxo-2H-[1,2,4]oxadiazolo[2,3-a]-s-triazin-7-yl}benzamide 5.0 g. of 7-amino-5-diallylamino-2H-[1,2,4]oxadiazolo[2,3-a]-s-triazin-2-one are mixed with 150 ml. of chloroform, 10 ml. of triethylamine and 4.5 ml. of 2,6-dichlorobenzoyl chloride and heated to reflux for 7 hours. The mixture is then cooled, diluted with water, adjusted to pH 4 with hydrochloric acid and extracted with chloroform. The combined organic extracts are dried over sodium sulfate and evaporated to dryness under reduced pressure. The residue is chromatographed over silica gel using a mixture of methylene chloride and methanol (99:1) for the elution. Recrystallization from diisopropyl ether and methylene chloride yields pure 2,6-dichloro-N-{5-diallylamino-2-oxo-2H-[1,2,4]oxadiazolo[2,3-a]-s-triazin-7-yl}benzamide having a melting point of 133°–135° C.

EXAMPLE 8

Preparation of pure
p-chloro-N-{5-diallylamino-2-oxo-2H-[1,2,4]oxadiazolo[2,3-a]-s-triazin-7-yl}benzamide 5.0 g. of 7-amino-5-diallylamino-2H-[1,2,4-a]-s-triazin-2-one are suspended in 7 ml. of triethylamine and 150 ml. of methylene chloride. 3.4 ml. of 4-chlorobenzoyl chloride in 35 ml. of methylene chloride are added dropwise while stirring and cooling to about 0° C. The mixture is subsequently stirred at about 0° C. for 1 hour. Water is then added thereto and the pH is adjusted to 4 with dilute hydrochloric acid solution. The two phases are separated and the aqueous phase is extracted twice with methylene chloride. The combined organic extracts are dried over sodium sulfate and evaporated to dryness under reduced pressure. The residue is recrystallized from methylene chloride and diethyl ether, there being obtained pure p-chloro-N-{5-diallylamino-2-oxo-2H-[1,2,4]oxadiazolo[2,3-a]-s-triazin-7-yl}benzamide having a melting point of 192°–194° C.

In an analogous manner, from 3.5 g. of 7-amino-5-diallylamino-2H-[1,2,4]oxadiazolo[2,3-a]-s-triazin-2-one and 2.2 ml. of 2-chlorobenzoyl chloride there was obtained pure o-chloro-N-{5-diallylamino-2-oxo-2H-[1,2,4]oxadiazolo[2,3-a]-s-triazin-7-yl}benzamide having a melting point of 179°–181° C.;

from 4.5 g. of 7-amino-5-diallylamino-2H-[1,2,4]oxadiazolo[2,3-a]-s-triazin-2-one and 3.2 ml. of 3-chlorobenzoyl chloride there was obtained pure m-chloro-N-{5-diallylamino-2-oxo-2H-[1,2,4]oxadiazolo[2,3-a]-s- triazin-7-yl}benzamide having a melting point of 172°–173° C.;

from 5.0 g. of 7-amino-5-diallylamino-2H-[1,2,4]oxadiazolo[2,3-a]-s-triazin-2-one and 5 g. of 2-acetylsalicylic acid chloride there was obtained pure o-{(5-diallylamino-2-oxo-2H-[1,2,4]oxadiazolo[2,3-a]-s-triazin-7-yl)carbamoyl}phenylacetate having a melting point of 159°–161° C.;

from 4.2 g. of 7-amino-5-diallylamino-2H-[1,2,4]oxadiazolo[2,3-a]-s-triazin-2-one and 3.1 g. of p-toluoyl chloride was obtained N-{5-diallylamino-2-oxo-2H-[1,2,4]oxadiazolo[2,3-a]-s-triazin-7-yl}-p-toluamide having a melting point of 151°–153° C.;

from 4.5 g. of 7-amino-5-diallylamino-2H-[1,2,4]oxadiazolo[2,3-a]-s-triazin-2-one and 3.4 g. of m-toluoyl chloride there was obtained N-{5-diallylamino-2-oxo-2H-[1,2,4]oxadiazolo[2,3-a]-s-triazin-7-yl}-m-toluamide having a melting point of 159°–160° C.;

from 4.5 g. of 7-amino-5-diallylamino-2H-[1,2,4]oxadiazolo[2,3-a]-s-triazin-2-one and 4.0 g. of anisoyl chloride there was obtained N-{5-diallylamino-2-oxo-2H-[1,2,4]oxadiazolo[2,3-a]-s-triazin-7-yl}-p-anisamide having a melting point of 185°–186° C.; and from 4.5 g. of 7-amino-5-diallylamino-2H-[1,2,4]oxadiazolo[2,3-a]-s-triazin-2-one and 3.0 g. of 4-cyanobenzoyl chloride there was obtained p-cyano-N-{5-diallylamino-2-oxo-2H-[1,2,4]oxadiazolo[2,3-a]-s-triazin-7-yl}benzamide having a melting point of 197°–199° C.

EXAMPLE 9

Preparation of pure N-{5-diallylamino-2-oxo-2H-[1,2,4]oxadiazolo[2,3-a]-s-triazin-7-yl}benzamide 7.0 g. of 7-amino-5-diallylamino-2H-[1,2,4]oxadiazolo[2,3-a]-s-triazin-2-one are suspended in 250 ml. of methylene chloride and 10 ml. of triethylamine, cooled while stirring to 0° C. and treated with 4.5 ml. of benzoyl chloride in 35 ml. of methylene chloride. The mixture is subsequently stirred at 0° C. for 1 hour, then diluted with water and adjusted to pH 4 with hydrochloric acid. The two phases are separated and the aqueous phase is extracted twice with methylene chloride. The organic extracts are combined, dried over magnesium sulfate and evaporated at 20° C. under reduced pressure. The residue is recrystallized from methylene chloride and diethyl ether, there being obtained pure N-{5-diallylamino-2-oxo-2H-[1,2,4]oxadiazolo[2,3-a]-s-triazin-7-yl}benzamide having a melting point of 182°–183° C.

EXAMPLE 10

Preparation of pure N-{5-diallylamino-2-oxo-2H-[1,2,4]oxadiazolo[2,3-a]-s-triazin-7-yl}benzamide 10.4 g. of 7-amino-5-diallylamino-2H-[1,2,4]oxadiazolo[2,3-a]-s-triazin-2-one are suspended in 300 ml. of methylene chloride and 12 ml. of triethylamine, cooled while stirring to 0° C. and treated with 10 g. of benzoic acid anhydride and 1.1 g. of 4-dimethylaminopyridine. The mixture is subsequently stirred at 0° C. for 45 minutes and then washed with water. The organic phase is dried over magnesium sulfate and concentrated. The crude product is recrystallized from methylene chloride and diethyl ether, there being obtained pure N-{5-diallylamino-2-oxo-2H-[1,2,4]oxadiazolo[2,3-a]-s-triazin-7-yl}benzamide having a melting point of 182°–183° C.

EXAMPLE 11

Preparation of N-{5-diallylamino-2-oxo-2H-[1,2,4]oxadiazolo[2,3-a]-s-triazin-7-yl}benzamide 3.3 g. of benzoic acid are dissolved in 70 ml. of methylene chloride and 2.7 g. of triethylamine. The solution is stirred and treated at 0° C. with 3.5 g. of isobutyl chloroformate in 25 ml. of methylene chloride. The mixture is then stirred at 0° C. for 30 minutes and subsequently at room temperature for 1 hour. The solution is treated with a suspension of 5 g. of 7-amino-5-diallylamino-2H-[1,2,4]oxadiazolo[2,3-a]-s-triazin-2-one in 200 ml. of methylene chloride, 12.5 ml. of triethylamine and 0.6 g. of 4-dimethylaminopyridine. The mixture obtained is stirred at room temperature for 18 hours and then washed with 100 ml. of water. The organic phase is dried over magnesium sulfate and evaporated under reduced pressure. The residue obtained is purified by column chromatography, there being obtained N-{5-diallylamino-2-oxo-2H-[1,2,4]oxadiazolo[2,3-a]-s-triazin-7-yl}benzamide having a melting point of 182°–183° C.

EXAMPLE 12

Preparation of the pure sodium salt of N-{5-diallylamino-2-oxo-2-H-[1,2,4]oxadiazolo-2,3-a]-s-triazin-7-yl}benzamide 4.5 g. of N-{5-diallylamino-2-oxo-2H-[1,2,4]oxadiazolo[2,3-a]-s-triazin-7-yl}benzamide are dissolved in 100 ml. of acetonitrile and treated with 12.8 ml. of 1-N sodium hydroxide. The mixture is concentrated under reduced pressure and the residue obtained is recrystallized from acetonitrile/water/diethyl ether, there being obtained the pure sodium salt having a melting point of 120°–130° C.

EXAMPLE 13

Preparation of the pure dicyclohexylamine salt of N-{5-diallylamino-2-oxo-2H-[1,2,4]oxadiazolo[2,3-a]-s-triazin-7-yl}benzamide 3.5 g. of N-{5-diallylamino-2-oxo-2H-[1,2,4]oxadiazolo[2,3-a]-s-triazin-7-yl}benzamide are dissolved in 50 ml. of acetonitrile and treated with 1.8 g. of dicyclohexylamine. Addition of diethyl ether leads to the precipitation of the pure dicyclohexylamine salt having a melting point of 141°–142° C.

EXAMPLE 14

Preparation the ethyldiisopropylamine salt of N-{5-diallylamino-2-oxo-2H-[1,2,4]oxadiazolo[2,3-a]-s-triazin-7-yl}benzamide 3.52 g. of N-{5-diallylamino-2-oxo-2H-[1,2,4]oxadiazolo[2,3-a]-s-triazin-7-yl}benzamide in 50 ml. of acetonitrile are treated with 1.3 g. of N-ethyldiisopropylamine in 50 ml. of acetontrile. The corresponding ethyldiisopropylamine salt having a melting point of 106°–108° C. precipitates upon adding diethyl ether.

EXAMPLE 15

Preparation of the corresponding salt of N-{5-diallylamino-2-oxo-2H-[1,2,4]oxadiazolo-[2,3-a]-s-triazin-7-yl}benzamide 3.52 g. of N-{5-diallylamino-2-oxo-2H-[1,2,4]oxadiazolo[2,3-a]-s-triazin-7-yl}benzamide in 50 ml. of acetonitrile are treated with 1.2 g. of tris(hydroxymethyl)aminomethane in 20 ml. of acetonitrile and 5 ml. of water. The corresponding salt having a melting point of 174°–175° C. precipitates after stirring for 30 minutes.

EXAMPLE 16

Preparation of pure
N-{5-diallylamino-2-oxo-2H-[1,2,4]oxadiazolo[2,3-a]-s-triazin-7-yl}propionamide 5 g. of 7-amino-5-diallylamino-2H-[1,2,4]oxadiazolo[2,3-a]-s-triazin-2-one are suspended in 80 ml. of methylene chloride and 5 ml. of triethylamine. 2.2 ml. of propionyl chloride in 20 ml. of methylene chloride are added dropwise at 0° C. The mixture is stirred for 90 minutes, then diluted with water, adjusted to pH 4 and extracted with methylene chloride. The combined organic extracts are dried over magnesium sulfate and evaporated under reduced pressure. The residue is chromatographed over silica gel using chloroform for the elution. Recrystallization from methylene chloride and diethyl ether yields pure N-{5-diallylamino-2-oxo-2H-[1,2,4]oxadiazolo[2,3-a]-s-triazin-7-yl}propionamide having a melting point of 157°–159° C.

In an analogous manner, from 4 g. of 7-amino-5-diallylamino-2H-[1,2,4]oxadiazolo[2,3-a]-s-triazin-2-one and 5 ml. of acetyl chloride there is obtained pure N-{5-diallylamino-2-oxo-2H-[1,2,4]oxadiazolo[2,3-a]-s-triazin-7-yl}acetamide having a melting point of 164°–165° C.;

from 3.6 g. of 7-amino-5-diallylamino-2H-[1,2,4]oxadiazolo[2,3-a]-s-triazin-2-one and 5 ml. of butyryl chloride there is obtained pure N-{5-diallylamino-2-oxo-2H-[1,2,4]oxadiazolo[2,3-a]-s-triazin-7-yl}butyramide having a melting point of 156°–158° C.; and from 5 g. of 7-amino-5-diallylamino-2H-[1,2,4]oxadiazolo[2,3-a]-s-triazin-2-one and 3.2 ml. of pivaloyl chloride there is obtained pure N-{5-diallylamino-2-oxo-2H-[1,2,4]oxadiazolo[2,3-a]-s-triazin-7-yl}pivalamide having a melting point of 129°–131° C.

EXAMPLE 17

Preparation of
N-{5-diallylamino-2-oxo-2H-[1,2,4]oxadiazolo[2,3-a]-s-triazin-7-yl}acetamide 6 g. of 7-amino-5-diallylamino-2H-[1,2,4]oxadiazolo[2,3-a]-s-triazin-2-one are stirred at room temperature for 18 hours with 60 ml. of absolute pyridine and 8 ml. of acetic acid anhydride. The solvents are distilled off at 40° C. and the residue is dissolved in 220 ml. of methylene chloride. The solution obtained is washed with 1-N-hydrochloric acid, dried over sodium sulfate and evaporated to dryness under reduced pressure. The residue is recrystallized from methylene chloride and diethyl ether, there being obtained N-{5-diallylamino-2-oxo-2H-[1,2,4]oxadiazolo[2,3-a]-s-triazin-7-yl}acetamide having a melting point of 164°–165° C.

EXAMPLE 18

Preparation of pure
N-{5-diallylamino-2-oxo-2H-[1,2,4]oxadiazolo[2,3-a]-s-triazin-7-yl}-2-furamide 6.0 g. of 7-amino-5-diallylamino-2H-[1,2,4]oxadiazolo[2,3-a]-s-triazin-2-one are suspended in 200 ml. of methylene chloride and 10 ml. of triethylamine. The mixture, cooled to about 0° C., is treated while stirring with 3 ml. of furan-2-carboxylic acid chloride in 50 ml. of methylene chloride. After stirring for 1 hour, the mixture is diluted with 100 ml. of water and adjusted to pH 4 with hydrochloric acid. The two phases are separated and the organic phase is dried over magnesium sulfate and evaporated under reduced pressure. The residue is recrystallized from methylene chloride and diethyl ether, there being obtained pure N-{5-diallylamino-2-oxo-2H-[1,2,4]oxadiazolo[2,3-a]-s-triazin-7-yl}-2-furamide having a melting point of 159°–162° C.

EXAMPLE 19

Preparation of pure
N-{5-diallylamino-2-oxo-2H-[1,2,4]oxadiazolo[2,3-a]-s-triazin-7-yl}nicotinamide dihydrochloride 4.5 g. of 7-amino-5-diallylamino-2H-[1,2,4]oxadiazolo[2,3-a]-s-triazin-2-one are suspended in 100 ml. of methylene chloride and 15 ml. of triethylamine. A suspension of 4.5 g. of nicotinoyl chloride hydrochloride in 50 ml. of methylene chloride is slowly added dropwise at 0° C. The dark solution is stirred at 0° C. for 2 hours, then washed twice with water and dried over sodium sulfate. The solvent is distilled off under reduced pressure and the residue is chromatographed over silica gel. The thus-obtained crude product is treated in methylene chloride with hydrochloric acid in dioxan, there being obtained pure N-{5-diallylamino-2-oxo-2H-[1,2,4]oxadiazolo[2,3-a]-s-triazin-7-yl}nicotinamide dihydrochloride having a melting point of 135°–140° C.

In an analogous manner, from 4.5 g. of 7-amino-5-diallylamino-2H-[1,2,4]oxadiazolo[2,3-a]-s-triazin-2-one and 4.5 g. of isonicotinoyl chloride hydrochloride there is obtained N-{5-diallylamino-2-oxo-2H-[1,2,4]oxadiazolo[2,3-a]-s-triazin-7-yl}isonicotinamide dihydrochloride having a melting point of 130°–140° C.;

from 3.6 g. of 7-amino-5-diallylamino-2H-[1,2,4]oxadiazolo[2,3-a]-s-triazin-2-one and 4.3 g. of 2-picolinoyl chloride hydrochloride there is obtained pure N-{5-diallylamino-2-oxo-2H-[1,2,4]oxadiazolo[2,3-a]-s-triazin-7-yl}-2-pyridinecarboxamide having a melting point of 213°–215° C.; and from 4.5 g. of 7-amino-5-diallylamino-2H-[1,2,4]oxadiazolo[2,3-a]-s-triazin-2-one and 2.4 ml. of thiophene-2-carboxylic acid chloride there is obtained pure N-{5-diallylamino-2-oxo-2H-[1,2,4]oxadiazolo[2,3-a]-s-triazin-7-yl}-2-thiophenecarboxamide having a melting point of 179°–181° C.

EXAMPLE 20

Preparation of
N-{5-diallylamino-2-oxo-2H-[1,2,4]oxadiazolo[2,3-a]-s-triazin-7-yl}-2-methoxyacetamide 5.0 g. of 7-amino-5-diallylamino-2H-[1,2,4]oxadiazolo[2,3-a]-s-triazin-2-one are suspended in 100 ml. of methylene chloride and 10 ml. of triethylamine. 2.5 g. of methoxyacetyl chloride in 20 ml. of methylene chloride are added dropwise while stirring and cooling to about 5° C. After 1 hour at about 5° C., the mixture is treated with water and adjusted to pH 4 with 3-N hydrochloric acid. The two phases are separated and the aqueous phase is extracted with methylene chloride. The combined organic extracts are dried over sodium sulfate and evaporated under reduced pressure. The residue is recrystallized from methylene chloride and diethyl ether, there being obtained N-{5-diallylamino-2-oxo-2H-[1,2,4]oxadiazolo[2,3-a]-s-triazin-7-yl}-2-methoxyacetamide having a melting point of 135°–136° C.

In an analogous manner, from 7.5 g. of 7-amino-5-diallylamino-2H-[1,2,4]oxadiazolo[2,3-a]-s-triazin-2-one and 2.9 ml. of chloroacetyl chloride there is obtained 2-chloro-N-{5-diallylamino-2-oxo-2H-[1,2,4]oxadiazolo[2,3-a]-s-triazin-7-yl}acetamide having a melting point of 159°-162° C.;

from 5.2 g. of 7-amino-5-diallylamino-2H-[1,2,4]oxadiazolo[2,3-a]-s-triazin-2-one and 2.6 g. of ethoxyacetyl chloride there is obtained 2-ethoxy-N-{5-diallylamino-2-oxo-2H-[1,2,4]oxadiazolo[2,3-a]-s-triazin-7-yl}acetamide having a melting point of 111°-113° C.; and from 4.8 g. of 7-amino-5-diallylamino-2H-[1,2,4]oxadiazolo[2,3-a]-s-triazin-2-one and 5.2 g. of phenoxyacetyl chloride there is obtained N-{5-diallylamino-2-oxo-2H-[1,2,4]oxadiazolo[2,3-a]-s-triazin-7-yl}-2-phenoxyacetamide having a melting point of 164°-166° C.

EXAMPLE 21

Preparation of pure N-{5-diallylamino-2-oxo-2H-[1,2,4]oxadiazolo[2,3-a]-s-triazin-7-yl}acrylamide 6.5 g. of 7-amino-5-diallylamino-2H-[1,2,4]oxadiazolo[2,3-a]-s-triazin-2-one are suspended in 120 ml. of methylene chloride and 8 ml. of triethylamine. 3 ml. of acrylyl chloride in 35 ml. of methylene chloride are added dropwise at 0° C. while stirring. The mixture is then stirred for 2 hours, diluted with 100 ml. of water and adjusted to pH 4 with 2-N hydrochloric acid. The two phases are separated and the aqueous phase is extracted with methylene chloride. The combined organic extracts are dried over sodium sulfate and evaporated to dryness under reduced pressure. The residue is chromatographed over silica gel using methylene chloride and methanol for the elution and the desired substance is recrystallized from methylene chloride and diethyl ether, there being obtained pure N-{5-diallylamino-2-oxo-2H-[1,2,4]oxadiazolo[2,3-a]-s-triazin-7-yl}acrylamide having a melting point of 157°-161° C.

In an analogous manner, from 5 g. of 7-amino-5-diallylamino-2H-[1,2,4]oxadiazolo[2,3-a]-s-triazin-2-one and 2.3 ml. of methacrylyl chloride there is obtained pure N-{5-diallylamino-2-oxo-2H-[1,2,4]oxadiazolo[2,3-a]-s-triazin-7-yl}-2-methylacrylamide having a melting point of 110°-112° C.;

from 4.5 g. of 7-amino-5-diallylamino-2H-[1,2,4]oxadiazolo[2,3-a]-s-triazin-2-one and 2.25 ml. of crotonyl chloride there is obtained N-{5-diallylamino-2-oxo-2H-[1,2,4]oxadiazolo[2,3-a]-s-triazin-7-yl}crotonamide having a melting point of 154°-157° C.;

from 4.5 g. of 7-amino-5-diallylamino-2H-[1,2,4]oxadiazolo[2,3-a]-s-triazin-2-one and 4.5 g. of cinnamoyl chloride there is obtained N-{5-diallylamino-2-oxo-2H-[1,2,4]oxadiazolo[2,3-a]-s-triazin-7-yl}cinnamic acid amide having a melting point of 215°-216° C.; and from 5.2 g. of 7-amino-5-diallylamino-2H-[1,2,4]oxadiazolo[2,3-a]-s-triazin-2-one and 4.0 g. of 3-(2-furyl)acrylyl chloride there is obtained N-{5-diallylamino-2-oxo-2H-[1,2,4]oxadiazolo[2,3-a]-s-triazin-7-yl}-2-furanacrylamide having a melting point of 224°-226° C.

EXAMPLE 22

Preparation of pure methyl N-{5-diallylamino-2-oxo-2H-[1,2,4]oxadiazolo[2,3-a]-s-triazin-7-yl}glutaramate 4.5 g. of 7-amino-5-diallylamino-2H-[1,2,4]oxadiazolo[2,3-a]-s-triazin-2-one are suspended with 10 ml. of triethylamine in 150 ml. of methylene chloride. The mixture is cooled while stirring and treated with 3.6 ml. of methyl (chloroformyl)butyrate. After stirring for 45 minutes, the mixture is diluted with water, adjusted to pH 4.5 with hydrochloric acid and extracted with methylene chloride. The combined organic extracts are dried over sodium sulfate and evaporated to dryness under reduced pressure. The crude product is chromatographed over silica gel using a mixture of chloroform and methanol (99:1) for the elution. Crystallization of the residue from methylene chloride and diethyl ether yields pure methyl N-{5-diallylamino-2-oxo-2H-[1,2,4]oxadiazolo[2,3-a]-s-triazin-7-yl}glutaramate having a melting point of 164°-165° C.

In an analogous manner, from 4.5 g. of 7-amino-5-diallylamino-2H-[1,2,4]oxadiazolo[2,3-a]-s-triazin-2-one and 2.15 ml. of methyl (chloroformyl)acetate there is obtained pure methyl N-{5-diallylamino-2-oxo-2H-[1,2,4]oxadiazolo[2,3-a]-s-triazin-7-yl}malonamate having a melting point of 138°-140° C.; and from 4.5 g. of 7-amino-5-diallylamino-2H-[1,2,4]oxadiazolo[2,3-a]-s-triazin-2-one and 3.6 ml. of methyl (chloroformyl)propionate there is obtained pure methyl N-{5-diallylamino-2-oxo-2H-[1,2,4]oxadiazolo[2,3-a]-s-triazin-7-yl}succinamate having a melting point of 129°-131° C.

EXAMPLE 23

Preparation of pure N-{5-diallylamino-2-oxo-2H-[1,2,4]oxadiazolo[2,3-a]-s-triazin-7-yl}glycine methyl ester 3.0 g. of 7-amino-5-diallylamino-2H-[1,2,4]oxadiazolo[2,3-a]-s-triazin-2-one are dissolved in 100 ml of acetone and treated with 4 ml. of methyl chloroacetate and 4 g. of potassium carbonate. The mixture is vigorously stirred for 21 hours and then evaporated to dryness under reduced pressure. The residue is dissolved in methylene chloride and water and extracted twice with methylene chloride. The combined organic extracts are dried over potassium carbonate and evaporated under reduced pressure. The crude product is chromatographed over silica gel using a mixture of methylene chloride and methanol (99:1) for the elution, there being obtained pure N-{5-diallylamino-2-oxo-2H-[1,2,4]oxadiazolo[2,3-a]-s-triazin-7-yl}glycine methyl ester which is recrystallized from acetone and petroleum ether; melting point 173°-174° C.

In an analogous manner, from 5 g. of 7-amino-5-diallylamino-2H-[1,2,4]oxadiazolo[2,3-a]-s-triazin-2-one and 7.8 ml. of ethyl 2-bromopropionate there is obtained pure N-{5-diallylamino-2-oxo-2H-[1,2,4]oxadiazolo[2,3-a]-s-triazin-7-yl}-DL-alanine ethyl ester having a melting point of 135°-137° C.; and from 5 g. of 7-amino-5-diallylamino-2H-[1,2,4]oxadiazolo[2,3-a]-s-triazin-2-one and 8.9 ml. of ethyl 2-bromobutyrate there is obtained pure ethyl rac-2-[(5-diallylamino-2-oxo-2H-[1,2,4]oxadiazolo[2,3-a]-s-triazin-7-yl)amino]butyrate having a melting point of 94°-95° C.

EXAMPLE 24

Preparation of dimethyl
{(5-diallylamino-2-oxo-2H-[1,2,4]oxadiazolo[2,3-a]-s-triazin-7-yl)imino}diacetate 3.0 g. of 7-amino-5-diallylamino-2H-[1,2,4]oxadiazolo[2,3-a]-s-triazin-2-one are dissolved in 120 ml. of acetone and treated with 6 ml. of methyl chloroacetate and 15 g. of potassium carbonate. The mixture is stirred for 52 hours and then evaporated to dryness. The residue is dissolved in methylene chloride and water and then extracted twice with methylene chloride. The combined organic extracts are dried over potassium carbonate and evaporated under reduced pressure. The residue is chromatographed over silica gel using a 0.5% mixture of methanol in methylene chloride for the elution, there being obtained dimethyl {(5-diallylamino-2-oxo-2H-[1,2,4]oxadiazolo[2,3-a]-s-triazin-7-yl)imino}diacetate. Pure substance is produced by recrystallization from diisopropyl ether; melting point 93°–95° C.

In addition, there is also obtained pure N-{5-diallylamino-2-oxo-2H-[1,2,4]oxadiazolo[2,3-a]-s-triazin-7-yl}glycine methyl ester having a melting point of 173°–174° C.

In an analogous manner, from 8.2 g. of 7-amino-5-diallylamino-2H-[1,2,4]oxadiazolo[2,3-a]-s-triazin-2-one and 22 ml. of ethyl bromoacetate there is obtained pure diethyl {(5-diallylamino-2-oxo-2H-[1,2,4]oxadiazolo[2,3-a]-s-triazin-7-yl)imino}diacetate having a melting point of 103°–104° C.; and from 3 g. of 7-amino-5-diallylamino-2H-[1,2,4]oxadiazolo[2,3-a]-s-triazin-2-one and 4 ml. of tert. butyl bromoacetate there is obtained di(tert.-butyl){(5-diallylamino-2-oxo-2H-[1,2,4]oxadiazolo[2,3-a]-s-triazin-7-yl)imino}diacetate having a melting point of 93°–95° C.

EXAMPLE 25

Preparation of pure ethyl
5-[3,6-dihydro-1(2H)-pyridyl]-2-oxo-2H-[1,2,4]oxadiazolo[2,3-a]-s-triazine-7-carbamate 4.8 g. of diethyl 6-[3,6-dihydro-1(2H)-pyridyl]-s-triazine-2,4-dicarbamate-3-oxide are mixed with 100 ml of absolute dimethylformamide and stirred at 140° C. for 30 minutes. The solvent is then evaporated off under reduced pressure and the residue is recrystallized from methylene chloride and diethyl ether, there being obtained pure ethyl 5-[3,6-dihydro-1(2H)-pyridyl]-2-oxo-2H-[1,2,4]oxadiazolo[2,3-a]-s-triazine-7-carbamate having a melting point of 220°–225° C.(decomposition).

In an analogous manner, from 4.8 g. of dimethyl 6-[3,6-dihydro-1(2H)-pyridyl]-s-triazine-2,4-dicarbamate-3-oxide there is obtained methyl 5-[3,6-dihydro-1(2H)-pyridyl]-2-oxo-2H-[1,2,4]oxadiazolo[2,3-a]-s-triazine-7-carbamate having a melting point of 217°–220° C.; and from 6.5 g. of diisobutyl 6-[3,6-dihydro-1(2H)-pyridyl]-s-triazine-2,4-dicarbamate-3-oxide there is obtained isobutyl 5-[3,6-dihydro-1(2H)-pyridyl]-2-oxo-2H-[1,2,4]-oxadiazolo[2,3-a]-s-triazine-7-carbamate having a melting point of 210°–215° C.(decomposition).

The diethyl 6-[3,6-dihydro-1(2H)-pyridyl]-s-triazine-2,4-dicarbamate-3-oxide used as the starting material can be prepared as follows:

300 g. of 2-chloro-4,6-diamino-s-triazine, 180 g. of 1,2,5,6-tetrahydropyridine and 170 g. of sodium bicarbonate are mixed in 1700 ml. of n-butanol and heated to reflux for 18 hours. The mixture is cooled and filtered. The residue is digested three times with hot chloroform and ethanol and filtered. The filtrates are combined and concentrated, there being obtained pure 2,4-diamino-6-[3,6-dihydro-1(2H)-pyridyl]-s-triazine having a melting point of 200°–202° C.

191 g. of m-chloroperbenzoic acid are dissolved in 800 ml. of dimethoxyethane and cooled to −5° C. 103 g. of 2,4-diamino-6-[3,6-dihydro-1(2H)-pyridyl]-s-triazine are then added in solid form within 2.5 hours. The mixture is left to warm to room temperature and then stirred overnight. The solvent is then concentrated at 20° C. under reduced pressure and 200 ml. of water are added. The pH value is then adjusted to 10 with sodium hydroxide and the solution is continuously extracted with chloroform for 20 hours. The solvent is then evaporated off and the crude product is chromatographed over silica gel, there being obtained pure 2,4-diamino-6-[3,6-dihydro-1(2H)-pyridyl]-s-triazine-3-oxide having a melting point of 261°–265° C.(decomposition).

The foregoing 3-oxide can also be obtained as follows:

40 g. of 1,2,5,6-tetrahydropyridine hydrochloride and 30 g. of sodium dicyanamide are suspended in 400 ml. of n-butanol and 30 ml. of water and heated to reflux overnight. The mixture is cooled and filtered and the filtrate is evaporated. The residue is digested in 100 ml. of water and the solid substance is filtered off and recrystallized from o-xylene, there being obtained pure 1-(1,2,5,6-tetrahydropyridine)-3-cyanoguanidine having a melting point of 131°–133° C.

60 g. of 1-(1,2,5,6-tetrahydropyridine)-3-cyanoguanidine are mixed with 1000 ml. of absolute tetrahydrofuran and 46 g. of potassium tert-butylate and heated to reflux for 5 minutes. The mixture is cooled to 5° C. and treated with 43 g. of cyanogen bromide, the temperature rising to 30° C. 46 g. of potassium tert. butylate are then added and the mixture is stirred at room temperature for 15 minutes. The solvent is then evaporated off under reduced pressure, the residue is dissolved in 500 ml. of water and treated with 28 g. of hydroxylamine hydrochloride. The mixture is then heated to reflux for 45 minutes. After cooling, the solution is made acid with hydrochloric acid and extracted twice with methylene chloride. The aqueous phase is then adjusted to pH 9 with sodium hydroxide and extracted with chloroform overnight. After evaporation of the solvent, there is isolated pure 2,4-diamino-6-[3,6-dihydro-1(H)-pyridyl]-s-triazine-3-oxide having a melting point of 260°–265° C.(decomposition).

10 g. of 2,4-diamino-6-[3,6-dihydro-1(2H)-pyridyl]-s-triazine-3-oxide are suspended in 350 ml. of methylene chloride and 40 ml. of triethylamine and cooled to 5° C. 10 ml. of ethyl chloroformate in 60 ml. of methylene chloride are slowly added dropwise while stirring. The mixture is stirred at 5° C. for 1 hour and at room temperature for 1 hour, washed with water and the aqueous phase is extracted with methylene chloride. The combined organic extracts are dried over sodium sulfate and evaporated under reduced pressure. The residue is recrystallized from methylene chloride and diethyl ether, there being obtained pure diethyl 6-[3,6-dihydro-1(2H)-pyridyl]-s-triazine-2,4-dicarbamate-3-oxide having a melting point of 143°–148° C.(decomposition).

In an analogous manner, from 6.2 g. of 2,4-diamino-6-[3,6-dihydro-1(2H)-pyridyl]-s-triazine-3-oxide and 6 ml. of methyl chloroformate there is obtained dimethyl 6-[3,6-dihydro- 1(2H)-pyridyl]-s-triazine-2,4-dicarbamate-3-oxide having a melting point of 190°–200° C.(decomposition); and from 5.8 g. of 2,4-diamino-6-[3,6-dihydro-1(2H)-pyridyl]-s-triazine-3-oxide and 7 ml. of isobutyl chloroformate there is obtained diisobutyl 6-[3,6-dihydro-1(2H)-pyridyl]-s-triazine-2,4-dicarbamate-3-oxide having a melting point of 133°–135° C.

EXAMPLE 26

Preparation of pure isobutyl 5-[3,6-dihydro-1(2H)-pyridyl]-2-oxo-2H-[1,2,4]oxadiazolo[2,3-a]-s-triazine-7-carbamate 8 g. of diisobutyl 6-[3,6-dihydro-1(2H)-pyridyl]-s-triazine-2,4-dicarbamate-3-oxide are dissolved in 300 ml. of methylene chloride and 1000 ml. of water and adjusted to pH 12.7 with concentrated sodium hydroxide. The mixture is stirred for 75 minutes, the organic phase is separated and the aqueous phase is adjusted to pH 4 with 3-N hydrochloric acid solution. The thus-obtained acidic aqueous solution is extracted with methylene chloride. The organic extracts are dried over sodium sulfate and evaporated, there being obtained pure isobutyl 5-[3,6-dihydro-1(2H)-pyridyl]-2-oxo-2H-[1,2,4]oxadiazolo[2,3-a]-s-triazine-7-carbamate having a melting point of 210°–215° C.

In an analogous manner, from diethyl 6-[3,6-dihydro-1(2H)-pyridyl]-s-triazine-2,4-dicarbamate-3-oxide there is obtained ethyl 5-[3,6-dihydro-1(2H)-pyridyl]-2-oxo-[1,2,4]oxadiazolo[2,3-a]-s-triazine-7-carbamate having a melting point of 220°–225° C.; and from dimethyl 6-[3,6-dihydro-1(2H)-pyridyl]-s-triazine-2,4-dicarbamate-3-oxide there is obtained methyl 5-[3,6-dihydro-1(2H)-pyridyl]-2-oxo-2H-[1,2,4]oxadiazolo[2,3-a]-s-triazine-7-carbamate having a melting point of 217°–220° C.

EXAMPLE 27

Preparation of pure 7-amino-5-[3,6-dihydro-1(2H)-pyridyl]-2-oxo-2H-[1,2,4]oxadiazolo[2,3-a]-s-triazin-2-one 9.5 g of 2,4-diamino-6-[3,6-dihydro-1(2H)-pyridyl]-s-triazine-3-oxide are suspended in 250 ml. of methylene chloride and cooled while stirring to 5° C. At this temperature there are simultaneously added dropwise within 30 minutes 25 ml. of 20% phosgene in toluene and 10% sodium hydroxide so that the pH is held at 7–8. The mixture is stirred for a further 1 hour and the two phases are separated. The aqueous phase is extracted twice with methylene chloride and methanol and the organic extracts are dried over magnesium sulfate. By evaporation of the solvent there is obtained pure 7-amino-5-[3,6-dihydro-1(2H)-pyridyl]-2-oxo-2H-[1,2,4]oxadiazolo[2,3-a]-s-triazin-2-one having a melting point of 220°–235° C. (decomposition).

EXAMPLE 28

Preparation of pure ethyl 5-[3,6-dihydro-1(2H)-pyridyl]-2-oxo-2H-[1,2,4]oxadiazolo[2,3-a]-s-triazine-7-carbamate 6.9 g. of 7-amino-5-[3,6-dihydro-1(2H)-pyridyl]-2-oxo-2H-[1,2,4]oxadiazolo[2,3-a]-s-triazin-2-one are suspended in 200 ml. of methylene chloride and 8 ml. of triethylamine and 5.2 ml. of ethyl chloroformate in 70 ml. of methylene chloride are added dropwise at 0° C., while stirring. After 1 hour at 0° C., the pH is adjusted to 4.5 with 1-N hydrochloric acid and the two phases are separated. The organic phase is dried over sodium sulfate and the solvent is distilled off. The residue is recrystallized from methylene chloride and diethyl ether, there being obtained pure ethyl 5-[3,6-dihydro-1(2H)-pyridyl]2-oxo-2H-[1,2,4]oxadiazolo[2,3-a]-s-triazine-7-carbamate having a melting point of 218°–225° C. (decomposition).

EXAMPLE 29

Preparation of pure N-{5-diallylamino-2-oxo-2H-[1,2,4]oxadiazolo[2,3-a]-s-triazin-7-yl}-2-thiophenacetamide 5.0 g. of 7-amino-5-diallylamino-2H-[1,2,4]oxadiazolo[2,3-a]-s-triazin-2-one are suspended in 100 ml. of methylene chloride and 10 ml. of triethylamine. 5.8 ml. of thiophen-2-acetyl chloride in 20 ml. of methylene chloride are added dropwise while stirring and cooling to about 0° C. The mixture is then stirred at about 5° C. for 4 hours, treated with water and adjusted to pH 3.7 with 3-N hydrochloric acid. The two phases are separated and the aqueous phase is extracted with methylene chloride. The combined organic phases are dried over sodium sulfate and evaporated under reduced pressure. The residue is chromatographed over silica gel with methylene chloride and methanol. Recrystallization from methylene chloride/diethyl ether yields pure N-{5-diallylamino-2-oxo-2H-[1,2,4]oxadiazolo[2,3-a]-s-triazin-7-yl}-2-thiophenacetamide having a melting point of 140°–142° C.

EXAMPLE 30

Preparation of pure N-{5-diallylamino-2-oxo-2H-[1,2,4]oxadiazolo[2,3-a]-s-triazin-7-yl}-3-thiophenacetamide 4.5 g. of 7-amino-5-diallylamino-2H-[1,2,4]oxadiazolo[2,3-a]-s-triazin-2-one are suspended in 100 ml. of triethylamine and 0.5 g. of 4-dimethylaminopyridine. 11.6 g. of thiophen-3-acetyl chloride in 40 ml. of methylene chloride are added dropwise while stirring and cooling to about 0° C. The mixture is then stirred at about 5° C. for 1 hour, treated with water and adjusted to pH 4 with 3-N hydrochloric acid. The two phases are separated and the aqueous phase is extracted with methylene chloride. The combined organic extracts are dried over magnesium sulfate and evaporated under reduced pressure. The residue is recrystallized from a small amount of methylene chloride and a large amount of diethyl ether, there being obtained pure N-{5-diallylamino-2-oxo-2H-[1,2,4]oxadiazolo[2,3-a]-s-triazin-7-yl}-3-thiophenacetamide having a melting point of 159°–161° C.

EXAMPLE 31

Preparation of pure N-{5-diallylamino-2-oxo-2H-[1,2,4]oxadiazolo[2,3-a]-s-triazin-7-yl}-3-methylcrotonamide 15 g. of 7-amino-5-diallylamino-2H-[1,2,4]oxadiazolo[2,3-a]-s-triazin-2-one are suspended in 300 ml. of methylene chloride, 30 ml. of triethylamine and 0.9 g. of 4-dimethylaminopyridine. 10.66 g. of 3,3-dimethylacrylyl chloride in 100 ml. of methylene chloride are added dropwise while stirring and cooling to about 5° C. The mixture is then stirred at 0° C. for 1 hour, treated with water and adjusted to pH 4 with 3-N hydrochloric acid. The two phases are separated and the aqueous phase is extracted with methylene chloride. The combined organic extracts are dried over magnesium sulfate and evaporated under reduced pressure. The residue is recrystallized from methylene chloride/diethyl ether, there being obtained pure N-{5-diallylamino-2-oxo-2H-[1,2,4]oxadiazolo[2,3-a]-s-triazin-7-yl}-3-methyl-crotonamide having a melting point of 165°–166° C.

EXAMPLE 32

Preparation of pure N-{5-diallylamino-2-oxo-2H-[1,2,4]oxadiazolo[2,3-a]-s-triazin-7-yl}-3-methylcrotonamide 22 g. of 7-amino-5-diallylamino-2H-[1,2,4]oxadiazolo[2,3-a]-s-triazin-2-one are suspended in 500 ml. of methylene chloride and 25 ml. of triethylamine. 19.6 g. of 3,3-dimethylacrylic acid anhydride in 400 ml. of methylene chloride are added at room temperature while stirring. The mixture is then stirred at room temperature for 90 minutes. The solution is then washed with water and subsequently with 3-N hydrochloric acid. The organic phase is dried over sodium sulfate and concentrated under reduced pressure. The residue is recrystallized from methylene chloride/diethyl ether, there being obtained pure N-{5-diallylamino-2-oxo-2H-[1,2,4]oxadiazolo[2,3-a]-s-triazin-7-yl}-3-methyl-crotonamide having a melting point of 165°–166° C.

The following Examples illustrate pharmaceutical preparations containing the oxadiazolotriazine derivatives of the invention:

EXAMPLE A

Tablets containing the following ingredients are produced:

| | | |
|---|---|---|
| I | N-{5-Diallylamino-2-oxo-2H-[1,2,4]-oxadiazolo[2,3-a]-s-triazin-7-yl}-benzamide (micronized) | 50.0 mg. |
| | Lactose (powdered) | 91.8 mg. |
| | Maize starch (white) | 75.0 mg. |
| II | Dioctyl sodium sulfosuccinate | 0.2 mg. |
| | Maize starch (white) | 8.0 mg. |
| | water | q.s. |
| III | Maize starch (white) | 20.0 mg. |
| IV | Talc | 4.0 mg. |
| | Magnesium stearate | 1.0 mg. |
| | | 250.0 mg. |

The ingredients of phase I are sieved and mixed. This mixture is moistened with the maize starch paste II and kneaded. The moist mass is granulated, dried and made into a suitable granular size. Phase III is admixed. The resulting mixture is mixed with phase IV for a further short time. The ready-to-press mixture is pressed to tablets weighing 250 mg. and having a diameter of 10 mm. and a break-bar.

EXAMPLE B

Tablets containing the following ingredients are produced:

| | | |
|---|---|---|
| I | N-{5-Diallylamino-2-oxo-2H-[1,2,4]-oxadiazolo[2,3-a]-s-triazin-7-yl}-benzamide (micronized) | 100.0 mg. |
| | Lactose (powdered) | 66.8 mg. |
| | Maize starch (white) | 50.0 mg. |
| II | Dioctyl sodium sulfosuccinate | 0.2 mg. |
| | Maize starch (white) | 8.0 mg. |
| | Water | q.s. |
| III | Maize starch (white) | 20.0 mg. |
| IV | Talc | 4.0 mg. |
| | Magnesium stearate | 1.0 mg. |
| | | 250.0 mg. |

The ingredients of phase I are sieved and mixed. This mixture is moistened with the maize starch paste II and kneaded. The moist mass is granulated, dried and made into a suitable granular size. Phase III is admixed. The resulting mixture is mixed with phase IV for a further short time. The ready-to-press mixture is pressed to tablets weighing 250 mg. and having a diameter of 10 mm. and a break-bar.

EXAMPLE C

Tablets containing the following ingredients are produced:

| | | |
|---|---|---|
| I | N-{5-Diallylamino-2-oxo-2H-[1,2,4]-oxadiazolo[2,3-a]-triazin-7-yl}-benzamide (micronized) | 250.0 mg. |
| | Lactose (powdered) | 83.6 mg. |
| | Maize starch (white) | 100.0 mg. |
| II | Dioctyl sodium sulfosuccinate | 0.4 mg. |
| | Maize starch (white) | 16.0 mg. |
| | Water | q.s. |
| III | Maize starch (white) | 40.0 mg. |
| IV | Talc | 8.0 mg. |
| | Magnesium stearate | 2.0 mg. |
| | | 500.0 mg. |

The ingredients of phase I are sieved and mixed. This mixture is moistened with the maize starch paste II and kneaded. The moist mass is granulated, dried and made into a suitable granular size. Phase III is admixed. The resulting mixture is mixed with phase IV for a further short time. The ready-to-press mixture is pressed to tablets weighing 500 mg. and having a diameter of 12 mm. and a break-bar.

EXAMPLE D

Injectable preparations containing the following ingredients are produced:

| | |
|---|---|
| N-{5-Diallylamino-2-oxo-2H-[1,2,4]oxadiazolo-[2,3-a]-s-triazin-7-7l}-benzamide | 50–250 mg. |
| Mannitol | 180–80 mg. |
| 2-N sodium hydroxide ad pH 12.3 | q.s. |
| 1-N hydrochloric acid ad pH 9.3 | q.s. |
| Water for injection | ad 5.0 ml. |

For the production of a finished injectable solution, the content of a dry ampul is dissolved in 4.9 ml. of water. 5.0 ml. of this solution contain 50–250 mg. of the N-{5-diallylamino-2-oxo-2H-[1,2,4]oxadiazolo[2,3-a]-s-triazin-7-yl}benzamide.

EXAMPLE E

Tablets or injectable preparations containing the following compounds or their pharmaceutically acceptable salts can be produced in a manner analogous to that described in Examples A to D:

N-{5-Diallylamino-2-oxo-2H-[1,2,4]oxadiazolo[2,3-a]-s-triazin-7-yl}-3-methylcrotonamide and
N-{5-diallylamino-2-oxo-2H-[1,2,4]oxadiazolo[2,3-a]-s-triazin-7-yl}-2-methylacrylamide.

We claim:
1. A compound of the formula

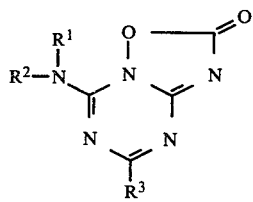

wherein $R^1$ is hydrogen, and $R^2$ is a group of the formula

—COOR$^5$ or —CH(R$^6$)COOR$^7$, or $R^1$ and $R^2$ are the same and are hydrogen or a group of the formula —CH(R$^6$)COOR$^7$, $R^3$ is diallylamino or 1,2,5,6-tetrahydropyridin-1-yl, wherein $R^4$ is alkyl of 1-8 carbon atoms, haloalkyl of 1-8 carbon atoms, alkoxy of 1-8 carbon atoms-alkyl of 1-8 carbon atoms, benzyloxyalkyl of 1-8 carbon atoms, phenethyloxy-alkyl of 1-8 carbon atoms, phenyloxy-alkyl of 1-8 carbon atoms, alkoxy of 1-8 carbon atoms-carbonylalkyl of 1-8 carbon atoms, benzyl, phenethyl, phenyl, halophenyl, dihalophenyl, methoxyphenyl, dimethoxyphenyl, nitrophenyl, tolyl, methoxycarbonylphenyl, naphthyl, a group of the formula —C(R$^8$)=CH(R$^9$), alkoxy of 1-8 carbon atoms-carbonylalkyl of 1-8 carbon atoms-carbonyl or a 4-membered to 7-membered heterocyclic group selected from the group consisting of furyl, nicotinyl, isonicotinyl, pyridyl, thienyl, pyrrolinyl and piperidinyl, which is optionally bound via a methylene group, $R^5$ is alkyl of 1-8 carbon atoms, alkoxy of 1-8 carbon atoms-alkyl of 1-8 carbon atoms, benzyl, phenethyl, phenyl, halophenyl, dihalophenyl, methoxyphenyl, dimethoxyphenyl, nitrophenyl, tolyl, methoxycarbonylphenyl, naphthyl or allyl, $R^6$ is hydrogen or alkyl of 1-8 carbon atoms, $R^7$ is alkyl of 1-8 carbon atoms and $R^8$ and $R^9$ each are alkyl of 1-8 carbon atoms, benzyl, phenethyl, phenyl, halophenyl, dihalophenyl, methoxyphenyl, dimethoxyphenyl, nitrophenyl, tolyl, methoxycarbonylphenyl, naphthyl, or a 4-membered to 7-membered heterocyclic group, selected from the group consisting of furyl, nicotinyl, isonicotinyl, pyridyl, thienyl, pyrrolinyl and piperidinyl, or a salt thereof with a pharmaceutically acceptable base.

2. A compound in accordance with claim 1, wherein $R^3$ is diallylamino.

3. A compound in accordance with claim 2, wherein $R^1$ is hydrogen and $R^2$ is hydrogen or a group of the formula

4. A compound in accordance with claim 3, wherein $R^4$ is benzyl, phenethyl, phenyl, halophenyl, dihalophenyl, methoxyphenyl, dimethoxyphenyl, nitrophenyl, tolyl, methoxycarbonylphenyl, naphthyl, alkoxy of 1-8 carbon atoms-alkyl of 1-8 carbon atoms, a group of the formula —C(R$^8$)=CH(R$^9$) or a 4-membered to 7-membered heterocyclic group selected from the group consisting of furyl, nicotinyl, isonicotinyl, pyridyl, thienyl, pyrrolinyl and piperidinyl which is optionally bound via a methylene group.

5. A compound in accordance with claim 4, wherein $R^4$ is phenyl, methoxymethyl, ethoxymethyl, the group of the formula —C(CH$_3$)=CH$_2$ or —C(CH$_3$)=CH—CH$_3$, or furyl.

6. A compound in accordance with any one of claims 1 to 5, wherein $R^3$ is diallylamino, $R^1$ is hydrogen, $R^2$ is hydrogen or a group of the formula

wherein $R^4$ is phenyl, methoxymethyl, ethoxymethyl, a group of the formula —C(CH$_3$)=CH$_2$ or —C(CH$_3$)=CH—CH$_3$, or furyl.

7. A compound in accordance with claim 1, N-{5-diallylamino-2-oxo-2H-[1,2,4]-oxadiazolo[2,3-a]-s-triazin-7-yl}benzamide.

8. A compound in accordance with claim 1, N-{5-diallylamino-2-oxo-2H-[1,2,4]-oxadiazolo[2,3-a]-s-triazin-7-yl}-2-methoxyacetamide.

9. A compound in accordance with claim 1, 2-ethoxy-N-{5-diallylamino-2-oxo-2H-[1,2,4]oxadiazolo[2,3-a]-s-triazin-7-yl}acetamide.

10. A compound in accordance with claim 1, N-{5-diallylamino-2-oxo-2H-[1,2,4]oxadiazolo[2,3-a]-s-triazin-7-yl}-2-methylacrylamide.

11. A compound in accordance with claim 1, N-{5-diallylamino-2-oxo-2H-[1,2,4]oxadiazolo[2,3-a]-s-triazin-7-yl}-2-furamide.

12. A compound in accordance with claim 1, 7-amino-5-diallylamino-2H-[1,2,4]-oxadiazolo[2,3-a]-s-triazin-2-one.

13. A compound in accordance with claim 1, N-{5-diallylamino-2-oxo-2H-[1,2,4]oxadiazolo[2,3-a]-s-triazin-7-yl}-3-methylcrotonamide.

14. A compound of the formula

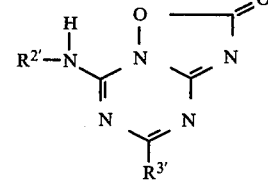

wherein $R^{2'}$ is a group of the formula

or —COOR$^{5'}$, wherein $R^{4'}$ is methyl, ethyl, propyl, chloromethyl, benzyl, p-chlorophenyl, 2,4-dichlorophenyl, 3,4-dichlorophenyl, p-tolyl, vinyl, propenyl, 2-(2-furyl)vinyl, 2-phenylvinyl, thienyl which is bound via a methylene group or 2-thienyl, and $R^{5'}$ is methyl, ethyl, butyl, isobutyl, 2-methoxyethyl, benzyl or allyl; and $R^{3'}$ is diallylamino.

15. A compound of the formula

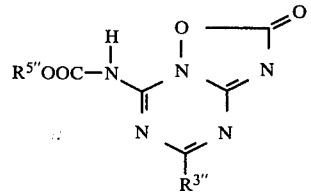

wherein $R''$ is 1,2,5,6-tetrahydropyridin-1-yl, and $R^{5''}$ is methyl, ethyl or isobutyl.

* * * * *